United States Patent
Denney (10) Patent No.: US 10,571,457 B2
(45) Date of Patent: *Feb. 25, 2020

(54) METHODS FOR THE DETECTION OF OXIDATIVE ADULTERANTS IN URINE SAMPLE

(71) Applicant: Vision Diagnostics, Inc.

(72) Inventor: Jerry W. Denney, Branford, FL (US)

(73) Assignee: VISION DIAGNOSTICS, INC., Branford, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/139,802

(22) Filed: Sep. 24, 2018

(65) Prior Publication Data

US 2019/0025284 A1 Jan. 24, 2019

Related U.S. Application Data

(63) Continuation of application No. 15/462,157, filed on Mar. 17, 2017, now Pat. No. 10,082,495.

(60) Provisional application No. 62/310,034, filed on Mar. 18, 2016.

(51) Int. Cl.
*G01N 33/493* (2006.01)
*G01N 21/78* (2006.01)
*G01N 21/31* (2006.01)

(52) U.S. Cl.
CPC ....... *G01N 33/493* (2013.01); *G01N 21/3103* (2013.01); *G01N 21/78* (2013.01); *Y10T 436/148888* (2015.01); *Y10T 436/16* (2015.01)

(58) Field of Classification Search
CPC .. G01N 21/3103; G01N 21/78; G01N 33/493; G01N 35/00; Y10T 436/145555; Y10T 436/147777; Y10T 436/148888; Y10T 436/16
USPC .... 436/16, 43, 63, 83, 96, 98, 99, 103, 164; 422/82.05, 82.09; 435/10
See application file for complete search history.

(56) References Cited

U.S. PATENT DOCUMENTS

| | | |
|---|---|---|
| 3,801,466 A | 4/1974 | Denney |
| 4,234,313 A | 11/1980 | Faulkner |
| 4,348,208 A | 9/1982 | Long |
| 6,303,384 B1 | 10/2001 | Mills et al. |
| 6,503,726 B2 | 1/2003 | Anne et al. |
| 7,445,908 B2 | 11/2008 | Paul |
| 10,082,495 B2* | 9/2018 | Denney ............... G01N 33/493 |
| 2003/0138959 A1 | 7/2003 | Carter et al. |

OTHER PUBLICATIONS

Dasgupta, A., "The Effects of Adulterants and Selected Ingested Compounds on Drugs-of-Abuse Testing in Urine," *Am J Clin Pathol*, 2007, pp. 491-503, vol. 128.

Folin, O., et al., "On Phosphotungstic-Phosphomolybdic Compounds as Color Reagents," *J. Bio. Chem.*, 1912, pp. 239-243, vol. 12.

Buchanan, O. et al., "The Metabolism of the Methylated Purines," *Journal of Biological Chemistry*, 1945, pp. 181-188, vol. 157.

Kwon, W. et al., "Simultaneous determination of creatinine and uric acid in urine by liquid chromatography-tandem mass spectrometry with polarity switching electrospray ionization," *Forensic Science International*, Apr. 12, 2012, pp. 57-64, vol. 221.

* cited by examiner

*Primary Examiner* — Maureen Wallenhorst
(74) *Attorney, Agent, or Firm* — Saliwanchik, Lloyd & Eisenschenk (57) ABSTRACT

The problem of confirming the presence of an adulterant in a urine sample is solved by the use of a reagent capable of reacting with uric acid and non-urate markers in a urine sample. In one embodiment, a phosphotungtate reagent is used to react with the urine sample to create a blue coloration in the presence of uric acid or uric acid equivalents. A reduction or elimination of the blue coloration, resulting in a reduction in the light absorbance, of the urine sample can be used as an indicator of the historical presence of an adulterant. An Oxidant History test can also be generated using the phosphostungtate reagent, wherein the light absorbance resulting from the blue coloration is measured over time, with a measured reduction in the absorbance being an indication that an adulterant is or has been present in the urine sample and is oxidizing the uric acid and non-urate markers over time.

16 Claims, 3 Drawing Sheets

METHODS FOR THE DETECTION OF OXIDATIVE ADULTERANTS IN URINE SAMPLE

CROSS-REFERENCE TO RELATED APPLICATION

This application is a continuation of U.S. application Ser. No. 15/462,157, filed Mar. 17, 2017, now U.S. Pat. No. 10,082,495, which claims the benefit of U.S. Provisional Application Ser. No. 62/310,034, filed Mar. 18, 2016, which is hereby incorporated by reference herein in its entirety, including any figures, tables, or drawings.

BACKGROUND OF INVENTION

Drug abuse is a critical problem throughout the world. Commonly abused drugs include cocaine, cannabinoids, amphetamine, phencyclidine (PCP), as well as designer drugs such as 3,4-methelenedioxyamphetamine (meth) 3,4-methelenedioxy-methamphetamine (Ecstasy) and others.

On Sep. 15, 1986, President Reagan issued Executive Order No. 12564 directing federal agencies to achieve a drug-free work environment. The Department of Health and Human Services (HHS) has developed guidelines and protocols for drugs-of-abuse testing. The mandatory Guidelines for Federal Workplace Drug Testing Programs were first published in the Federal Register on Apr. 11, 1988, and that were since revised on Jun. 9, 1994, and on Sep. 30, 1997. Another notice was issued on Apr. 13, 2004.

It is estimated that approximately 20 million employees are screened each year for illicit drug use. Drug testing programs in the United States can be classified as mandatory or non-mandatory. In the mandatory programs (e.g., the Department of Transportation), a regulated employer is required by federal regulation to test employees. In the non-mandatory programs, employers choose to test for reasons other than federal regulations.

Persons using drugs may attempt to adulterate urine specimens to avoid detection. Adulterants are substances that can be added to a urine sample to affect the integrity of the sample and results of the laboratory assays used to detect drugs of abuse (DOA). These adulterants are often oxidants that destroy, or partially destroy, evidence of DOA in a urine sample. Thus, both screening and confirmatory tests can be rendered negative. Oxidant adulterants include potassium nitrite (e.g., "Klear" and "Whizzies"), potassium chlorochromate (e.g., "Urine Luck") and hydrogen peroxide/peroxidase (e.g., "Stealth") and are readily available, usually at low cost. Household bleach is also an effective adulterant that can cause negative DOA results. Adulterants can degrade and disappear in a sample within hours after being added, making them difficult or impossible to detect. Further, specific tests have to be conducted to detect each type of adulterant.

DOA testing often involves several steps, which can include: (a) sample collection, (b) sample integrity testing, (c) DOA Screening, and (d) confirmatory tests. These steps may: (a) occur at different locations, (b) be conducted by personnel with varying qualifications, (c) be conducted by different institutions, and/or (d) be conducted sequentially at different times. For example, confirmatory tests are conducted after the screening tests and often required that the sample be transported from one institution or laboratory to another. The steps leading to the confirmatory testing step may occur over one or more days.

Laboratories typically screen samples using commercially available enzyme immunoassays (EIA) and related methods and reagents. These screening methods are not always completely specific as there can be cross-reacting substances that can cause false positive results. Consequently, cut-off values or minimum concentrations for each drug have been established, whereby assayed values below the cut-off value are considered negative results. If a positive result is obtained by the EIA screen, the sample can be sent to a confirmatory testing laboratory where Liquid or Gas Chromatography/Mass Spectrophometry equipment is often utilized for the confirmatory test. Generally, the cut-off values used for the confirmatory test are lower than the values used for the initial screening (EIA). In general, only initially positive screening tests are submitted for confirmatory testing and the confirmatory test results are considered conclusive. Because of the cut-off value criteria used to establish a positive result in these tests, adulterants only need to lower the tested value of the urine sample below the cut-off level to produce an accepted negative result.

Federal guidelines by the U.S. NRC, 10 CFR 26.161 require that specimen integrity tests be performed by HHS-certified laboratories. Clinical laboratory professional organizations have called attention to the problems with adulterated urine samples for illicit drug testing; however, detecting an adulterated urine sample is difficult. The American Journal of Clinical Pathology concluded that new adulterants can produce false negative results for DOA. The Substance Abuse and Mental Health Services Administration (SAMHSA) reports that of 6,320,000 samples tested in 2013 one of every 300 was invalid. If the adulterant testing procedures failed to detect "disappearing" adulterants, that number may have been even higher. The invalid tests may also be much higher in non-mandated labs or other labs not performing adequate tests for adulterants.

Manual spot tests have become available to test for the presence of adulterants in a sample. Although a step in the right direction in detecting adulterants, these tests can be laborious and expensive to perform and primarily provide only qualitative results, which may still result in underdetection or false positives. The high cost of these manual tests may lead non-mandated laboratories to take short cuts in adulterant testing, partially because reimbursement for adulterant testing has been uncommon. Recently the reimbursement for DOA testing has been reduced with the reimbursement for confirmatory testing reduced more than that for EIA screening tests. Previously, some adulterant testing was reimbursed; but, under the new reimbursement for DOA the adulterant screening is included in the reimbursement for DOA testing. It appears that now, labs not doing adulterant screening are not doing all of the testing for which they are paid. Adulterant testing products and labor can be costly, and the cost is escalating, causing non-mandated laboratories to forego adulterant testing. Ironically, clinical laboratory testing costs in general are one of the few areas in health care where costs of an individual diagnostic test have declined since the 1950's. That reduction in cost has been brought about by laboratory automation and the integration of the automation with laboratory/hospital information systems. The use of automated systems, methods, and reagents combined with automated sample identification and documentation by an integrated Laboratory Information System computer would enable the costs to be reduced to a fraction of the costs of manual adulteration spot test, if a reagent were available.

A wide variety of oxidative-adulterants is available that can avoid detection of DOA, and new ones are regularly introduced into the market. Testing all samples for specific oxidants would be very expensive. As such, ideally a general oxidant-screening test could be used to determine and provide evidence that an oxidative-adulterant may have been used to adulterate a sample, as opposed to testing samples for the presence of specific adulterants.

Prior art automated screening for oxidant adulteration employs General Oxidant detecting reagents, which are intended to detect the presence of an oxidative-adulterant; however, nitrite, a commonly used oxidant adulterant, may be naturally present in low concentration in urine due to, for example, a bacterial presence in the urinary tract or use of certain therapeutic drugs. Consequently, in an effort to minimize or inhibit these samples from being tested positive for DOA, the tests use an oxidizing equivalence of 200-500 units of nitrite as a lower cutoff level.

In addition, adulterant testing can be performed by the confirmatory laboratory hours or days after an adulterant would have been added to the sample. Because of the multiple steps in the DOA testing process, the result can be positive at the time of testing by the screening lab, but negative when tested some time later by the confirmatory lab. This can allow an adulterant, such as STEALTH™, to degrade or "disappear" to a level below those above-mentioned by the time testing is conducted. Thus, such a sample can pass adulteration screening tests for a General Oxidant. Further, the adulterant may continue to destroy the drug of abuse during the delay period before disappearing, thereby avoiding detection of both in the screening tests.

As previously indicated, new adulterants are being introduced periodically. Stealth-type products (which include hydrogen peroxide+peroxidase) are known to effectively escape detection. It is therefore likely that other types of oxidants having the "disappearing" nature of Stealth will be favored by those profiting from the sale and use of adulterants.

BRIEF SUMMARY

The subject invention provides methods and reagents useful for analysis of urine samples to detect the historical presence of an oxidant, such as those that are often used to mask Drugs-of-Abuse (DOA). In particular, the subject invention provides reagents and methods for the detection of chromogenic markers in a urine sample, which can be used as indicators of the presence of oxidative-adulterant(s) having been added to the sample. The subject invention further provides a method by which the use of an oxidative-adulterant can be confirmed by later confirmatory testing of the urine sample. The embodiments of the subject invention further include methods by which standard laboratory automation equipment or clinical analyzers can be used to detect the effect of oxidative-adulterants on the markers, thereby facilitating automated urine sample analysis for adulterant detection. Specifically, spectrophotometry analysis of a sample reacted with the embodiments of the reagents of the subject invention can indicate whether a sample contains or had contained an oxidant, which can further indicate the current or past presence of an adulterant in the sample. More specifically, a reduction in light absorbance of the sample within a particular wavelength range can indicate that the markers have been oxidized, which can further indicate the historical presence of an adulterant in the sample.

Advantageously, the methods of the subject invention detect adulteration of a urine sample by measuring the effects of the oxidative-adulterant on compounds or markers that are stable and consistently present in urine, which can be more effective and reliable than detecting and/or measuring the actual presence of the oxidant. In one embodiment, the methods and reagents of the subject invention are used to obtain a measure of the amount of, or value of, the markers in a urine sample. If the measurement, or value, is below the accepted cut-off level for normal human urine, it means that the markers have been oxidized. Because the selected markers tend to be stable in urine, a lower than normal measure or value of the markers is a definitive indication that the urine sample was adulterated with a substance capable of oxidizing the DOA and also the markers.

In a particular embodiment, the methods of the subject invention can be used to create an Oxidant History (OHist), which utilizes two or more marker values to demonstrate whether there are historical changes in the sample markers during a pre-determined time window. Advantageously, the results of the tests obtained with the methods and reagents of the subject invention can be unaffected by the timing of the tests and are further suitable for use in analysis with automated laboratory equipment. The initial physical change and concentration of the markers caused by the presence of an oxidant-adulterant can remain stable over time. If the concentration of the markers does change, it can reinforce or confirm the presence of an oxidant and adulteration of the urine sample. Advantageously, the marker(s) utilized are naturally present in urine of all primates, including humans.

In one embodiment, uric acid is utilized as a marker in a urine sample. In a further embodiment, a phosphotungstate reagent is used to detect the amount of uric acid in the sample. However, phosphotungstate lacks specificity for detection of uric acid. This is believed to be due to the presence of low levels of secondary compounds or constituents, which can be referred to as "non-urate markers" that are found in biological fluids such as urine. These other constituents include, but are not limited to, ascorbic acid, cystine, cysteine, ergothioneine, and glutathione. These constituent substances were discovered to also be oxidized by oxidizing adulterants. The method of the subject invention advantageously employs, or is at least not inhibited by, this lack of specificity of phosphotungstate can use these constituents beneficially for the indirect detection of oxidizing-adulterants in urine.

It has also been discovered that in the presence of uric acid and other non-urate constituents in urine the phosphotungstate can be a chromogen. Specifically, the phosphotungstate reagent can react with these constituents causing urine to turn a blue color, thus enabling a combined quantification of these substances. Therefore, according to the present invention, the non-urate markers can be treated as being equivalent to uric acid for the purposes of analysis. The subject invention can utilize the oxidation of both these non-urate markers and uric acid markers by the oxidizing adulterant to obtain a single value for analysis, generally referred to herein as a Uric Acid Equivalent. Thus, as used herein, a value for the Uric Acid Equivalent refers to the amount of both uric acid and non-urate markers in a sample of bodily fluid, such as, for example urine. In one embodiment, a visual determination can be made of the amount of Uric Acid Equivalents. For example, the sample color can be compared to a color guide or other visual guide to determine the amount of Uric Acid Equivalents in the sample. Advantageously, the embodiments of the subject invention can be used with colorimetric techniques and spectrophotometric devices that can more accurately and easily quantify the amount of Uric Acid Equivalents in the sample of bodily fluid, such as, for example, urine.

The addition of oxidative-adulterants, which normally inhibit drug measurement in urine by oxidatively destroying the drugs, can also oxidize uric acid and non-urate markers. The oxidation of these markers can significantly affect their ability to react and form a blue color reaction with the phosphotungstate reagent of the present invention. More specifically, the presence of an oxidative-adulterant can reduce or lighten the blue color formation and, at certain concentrations, an oxidative-adulterant can eliminate most or all of the blue color that can normally be produced by the presence of Uric Acid Equivalent markers in the urine to react with the phosphotungstate. This can result in a reduction in light absorbance at certain wavelengths during colorimetric or spectrophotometric analysis.

Figure 1:
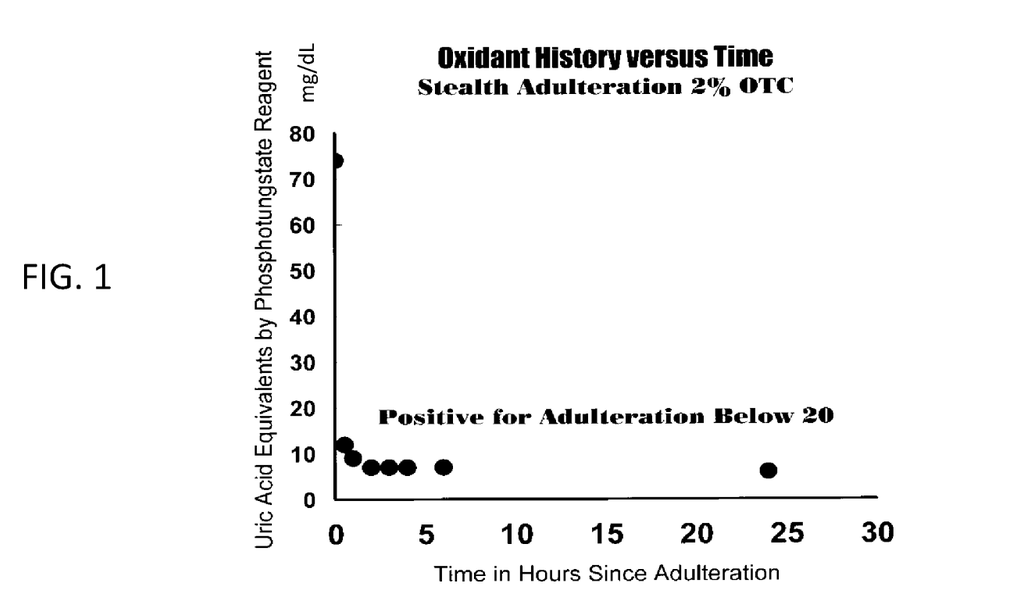
FIG. 1 is a graph of an Oxidant History of Uric Acid Equivalents in a urine sample that has been adulterated with the STEALTH, a commercially-available adulterant.
Figure 2:
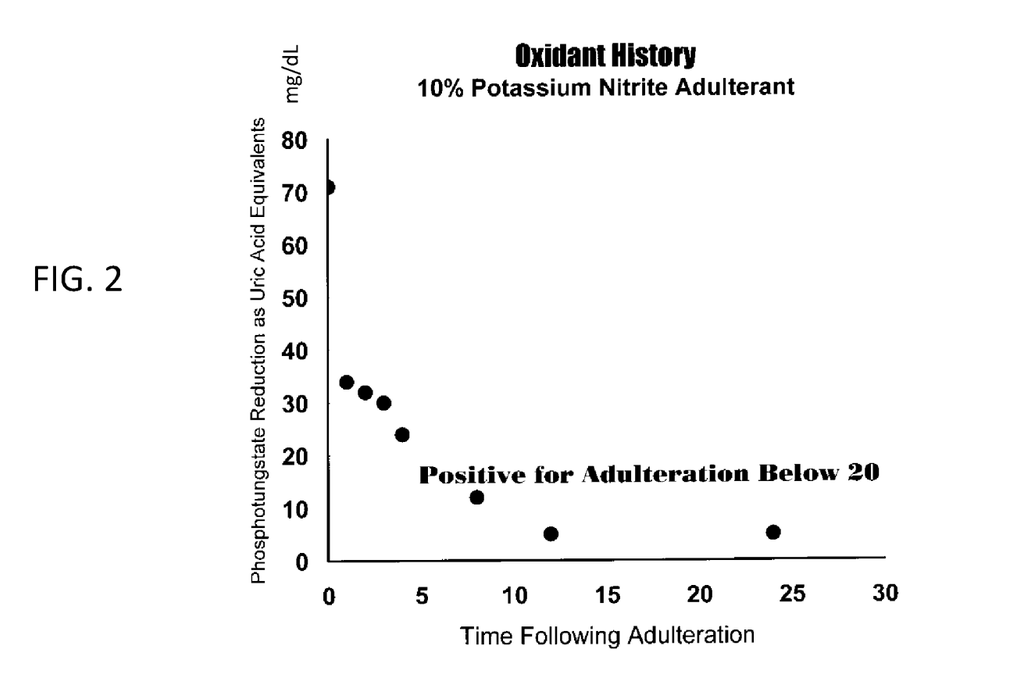
FIG. 2 is a graph of an Oxidant History of Uric Acid Equivalents in a urine sample that has been adulterated with a 10% potassium nitrate.
Figure 3:
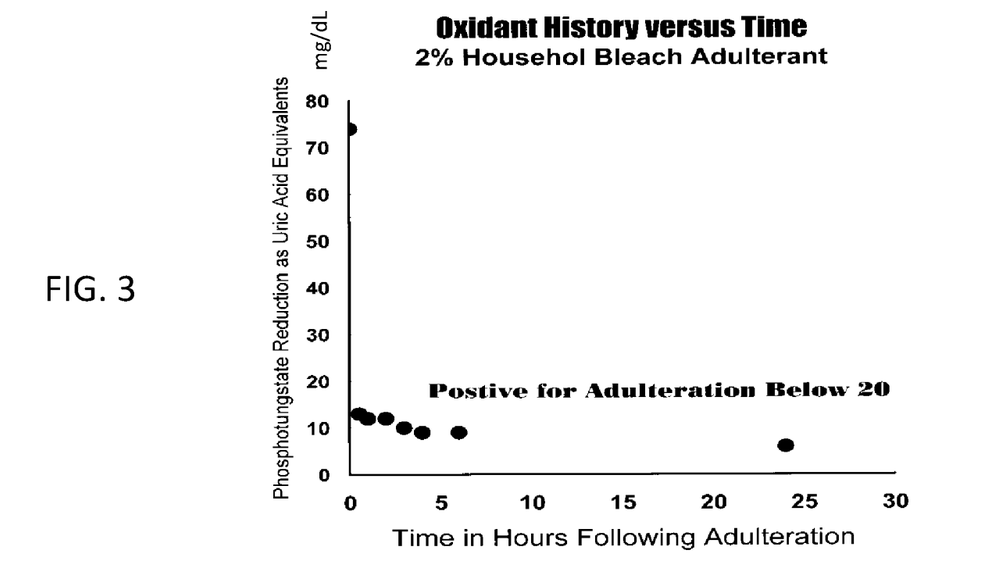
FIG. 3 is a graph of an Oxidant History of Uric Acid Equivalents in a urine sample that has been adulterated with 2% bleach.

Commonly used oxidants such as, but not limited to, nitrite, bleach (chlorine), and the product "Stealth" can destroy these markers in urine, which reduces or inhibits the reaction with the phosphotungstate reagent. Thus, the previously perceived disadvantages of using phosphotungstate reduction reaction due to "inaccuracy" of the results in quantifying only uric acid, becomes an advantage with the subject invention. The ability to use more than one marker to reduce the phosphotungstate is useful for revealing the oxidative effects of the adulterants, as shown, for example, in FIG. 1, FIG. 2, and FIG. 3.

It has been further discovered that the reaction and subsequent color of a phosphotungstate-treated urine sample, can remain stable for several hours or days, in the absence of an oxidizer. In other words, the color of a urine sample can experience minimal or no change after the initial reaction is complete, if there is no oxidizing substance in the sample. Thus, the integrity of the urine sample and the markers can remain stable over time. However, if the initial value of Uric Acid Equivalents is below normal levels for human urine, the sample can be retested without concern that the markers were adversely affected over time. However, any continued loss of intensity of the blue color, thus causing reduction in light absorbance, in later confirmatory testing can be a further confirmation of the presence of an oxidative-adulterant that has continued oxidation of the markers in the sample over time. This is because such a reduction in the markers that comprise the Uric Acid Equivalents can only occur in the presence of an oxidative substance, which can be a definitive indication that an adulterant is, or was, present in the sample.

By contrast, the General Oxidant tests or tests currently known and used in the art, to directly detect the presence of an oxidative-adulterant, can produce a false negative result for the presence of an oxidative-adulterant. This is because many adulterants can degrade over time, making them undetectable by certain tests, such as tests that attempt to directly detect an oxidative-adulterant. Thus, even if a test to detect an oxidative-adulterant is conducted shortly after collection, even in as little as 1 hour after adulteration of the sample, it may not be detected due to the "disappearing" or degrading nature of the oxidative-adulterant.

In another embodiment of the subject invention, an Oxidant History (OHist) is prepared that can further indicate or confirm the historical presence of an oxidative-adulterant. By obtaining colorimetric or spectrophotometric measurements of the Uric Acid Equivalents utilizing the blue urine color over a predetermined period of time, the method of the subject invention can provide a history of the levels of the markers over time. The measurements or values of these markers and changes thereof can be an indication of the continued operation of an oxidizing-adulterant in the sample. It can also be used to explain the lack of detection of DOA by a confirmatory testing.

Thus, with the embodiments of the subject invention, the preparation of an OHist utilizing the embodiments of the phosphotungstate reagent of the subject invention meets the need for a more complete screening method for detecting the historical presence of oxidative-adulterants including those known to "disappear" from a sample, such as, for example. Stealth and Stealth-type adulterants. The detection of the possible use of oxidative-adulterants, such as Stealth, is important because of the effectiveness of this type adulterant both in producing false negative drug tests, and also for the number of drugs for which they are capable of producing false negatives results. Further, because they can continue to affect a urine sample, even after the initial screening test, oxidative-adulterants, like Stealth, can mask DOA both initially (usually after enzyme immunoassay testing) and during later confirmatory tests (such a gas chromatography/mass spectrometry).

The confirmatory tests available for detecting specific oxidative-adulterants can be utilized in conjunction with the embodiments of the subject invention. However, with the embodiments of the subject invention, the battery of tests required to confirm the presence of an oxidative-adulterant may only need to be conducted on samples that present an initially positive result for value of Uric Acid Equivalents screening test. The ability to integrate the reagent and the method of the subject invention with automated laboratory testing equipment, such as clinical analyzers, can further reduce costs and increase the speed at which such test can be performed.

In one embodiment, screening tests are performed to obtain an initial screening value of Uric Acid Equivalents for all samples. Confirmatory testing can be performed on the subset of samples that test positive for oxidative adulteration, pursuant to the results of the initial screening value of Uric Acid Equivalents being below the normal cut-off level. The confirmatory test procedure can produce another Uric Acid Equivalent value that, can be used with the initial screening Uric Acid Equivalent value to provide an OHist. The OHist can be a further definitive indicator as to whether an oxidative-adulterant was used in the urine sample. The ability of the subject invention to more accurately target suspect urine samples can further limit the number of confirmatory screening tests performed. This can provide a reduction in the overall number of confirmatory screening tests that need to be performed, which can also reduce the overall cost associated with confirmatory testing.

Obtaining an initial value of Uric Acid Equivalents can be an effective means for reducing the risk to a testing laboratory. Oxidant adulterants can be of low concentration or strength and therefore be slow acting and not provide an initial indication of the presence of DOA. However, other screening tests for DOA that produce an initially positive result but that fail to be confirmed by a subsequent confirmatory laboratory, such as, for example, with Gas Chromatography/Mass Spectrometer (GG/MS) procedures, can be retested to obtain one or more additional Uric Acid Equivalent values. An OHist can be prepared by comparing the original Uric Acid Equivalent value, taken during the initial screening, to the one or more additional Uric Acid Equivalent values obtained by the confirmatory laboratory. If the OHist demonstrates that there was a significant decrease in Uric Acid Equivalents values over the time window during which the sample was tested, it would be an indication that the sample was adulterated with an oxidative-adulterant. In this situation, the DOA was likely present during the screening test and had been oxidized by the time the GC/MS test was performed. As discussed above, the failure of the confirmatory laboratory to detect the DOA could be due to the disappearance of the adulterant by the time the sample was subject to testing.

Ideally, a Uric Acid Equivalent or OHist test that the laboratory considers borderline or otherwise suspicious should be retested 24 hours after collection. The oxidant time-history of a sample, as provided by the OHist testing procedures of the subject invention, can provide definitive confirmation of oxidant adulteration of a urine sample. An OHist, as used herein, refers to obtaining historical measurements of Uric Acid Equivalents values in a sample over a pre-determined period of time or during a time window. These measurements can be used to prepare an OHist for the given time window, which can be a history of the effects of an oxidative-adulterant on a urine sample. As discussed above, the OHist can show how an oxidant adulterant in a urine sample progressively destroys the phosphotungstate-reducing ability of the markers in the urine sample, thereby affecting the light absorbance of the sample at certain wavelengths. Although the initial decrease can be substantial, as indicated by the graphs in FIGS. 1, 2, and 3, the effects can continue, often more slowly, over time.

A low cut-off limit can be established to inhibit false positive results, but which can also produce false negative results. However, with the embodiments of the subject invention, an oxidative-adulterant that can affect measurements of samples treated with the phosphotungstate reagent of the subject invention can be more easily detected by confirmation testing when conducted at a later time. Absent the presence of oxidative-adulterants, the levels of uric acid in urine are known to be very stable for a relatively long time period, at least several days. The confirmation test can be carried out by re-assaying and observing the changes in the level of reduction capacity of the phosphotungstate reagent, which can only be caused by the presence in the sample of an oxidative-adulterant affecting the markers that make up the Uric Acid Equivalent value. A significant lowering of the phosphotungstate reduction capacity of the urine sample, as indicated by a reduction in the blue coloration of the urine, can thus be a definitive confirmation of the presence of oxidative adulterant, regardless of the original uric acid concentration. Thus, the measurement of phosphotungstate reduction or the levels of the markers, and changes therein, can be useful in both a screening test and a confirmation test.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which.

DETAILED DISCLOSURE

The subject invention pertains to an assay reagent and methods of use for detecting a decrease in specific markers present in a urine sample. In specific embodiments, the subject invention provides an assay reagent that reacts with uric acid and non-urate constituents found normally in urine. The methods described herein can be useful for determining whether a urine sample has been treated with an oxidative-adulterant. The methods and reagents of the subject invention can provide a visually detectable and quantifiable result. Advantageously, the embodiments of the subject invention can also be incorporated with standard automated laboratory equipment, such as clinical analyzers, utilized to conduct automated testing of urine samples for Drugs of Abuse (DOA).

The subject invention is particularly useful in the field of laboratory screening and testing of urine samples, more particularly, the procedures used to test for the presence of an adulterant used to mask the presence of DOA. While the subject application describes, and many of the terms herein relate to, a use for detection of urine sample adulterants that mask DOA, other modifications apparent to a person with skill in the art and having benefit of the subject disclosure are contemplated to be within the scope of the present invention.

Currently, both Immunoassay Laboratories and Confirmatory Labs using GC/MS can report contradictory results, usually due to a positive DOA test being reported by the Immunoassay Laboratories followed by a negative DOA test in the Confirmatory Lab. This result is usually attributed to greater specificity for DOA assay by GC/MS and known cross-reactants causing false positives in the initial immunoassay tests. In some cases, this may be the cause; however, it has been shown that this may also be due to slow oxidation of uric acid and non-urate constituents in the sample by an oxidative adulterant. By using the methods and reagents of the subject invention, such results can be used to indicate that (a) the sample was adulterated and (b) that the first immunoassay result was more likely to be correct.

In certain embodiments, the subject invention provides a phosphotungstate reagent and method that can be more accurate than the current assay reagents and methods used to detect DOA in urine samples. The phosphotungstate reagent operates by reacting with the normally-occurring uric acid and non-urate markers. In the presence of these markers, the phosphotungstate reagent is reduced, which creates a blue coloration in the urine sample. It has been found that these markers are also affected by the presence of adulterants in the urine, which also oxidize these markers. As such, these markers can be used in the practice of the subject invention. When oxidized, the markers are inhibited from reacting with the phosphotungstate reagent thereby decreasing or preventing the blue coloration. These markers are generally stable in urine and will not oxidize under normal conditions. Thus, a reduction or lack of blue coloration in a urine sample treated with the phosphotungstate reagent of the subject invention is an indication of the presence of an oxidant destroying or inactivating the markers, which could indicate use of an adulterant.

The blue coloration, when analyzed spectroscopically, can indicate the concentration of markers present in the urine sample. In one embodiment, the blue coloration affects light absorbance in the range of from between approximately 580 to approximately 800 nm. In a more particular embodiment, the blue coloration affects light absorbance in the range of from between approximately 600 to approximately 700 nm. In a specific embodiment, the blue coloration affects light absorbance in the range of from between approximately 650 nm to approximately 700 nm.

An initial test result where the amount of available marker is below the established cut-off levels can be a definitive indication that an oxidative-adulterant is present or was historically present in the sample. Advantageously, the effect of an oxidant-adulterant on a urine sample can be enhanced or can continue over time. Thus, the presence of an oxidative-adulterant in a urine sample can further oxidize these markers over time. Thus, when subject to confirmatory testing, if the test results obtained for a sample show that the available markers are less than those from earlier test results obtained from the initial screening test, i.e., the blue coloration is further reduced in the sample, the presence of an oxidant adulterant in the sample is definitively indicated.

In a further embodiment, an Oxidant History (OHist) can also be obtained for samples, allowing an initial test result to be compared to later test results. The results of the OHist can be used as effective evidence of the presence of an adulterant in a urine sample. A further embodiment provides a method by which an OHist can be established if a second test result is below the established cut-off value for the markers in a urine sample.

The level of uric acid can vary between samples. However, the embodiments of the subject invention can still be effective because the effects of the oxidative-adulterants can still reduce the blue color in a sample to levels that are far lower than the lowest range possible of even pathologically lowered human urine. Diseases that lower uric acid levels are rare. Friedman & Young report only 5 relatively-uncommon diseases capable of causing lowered uric acid levels while reporting 40 more common diseases that are capable of elevating uric acid levels. [Friedman, R. B. and Young, D. S.; Effects of Disease on Clinical Laboratory Tests, Second Edition, pp. 3-(232-232); AACC Press, 2029 K Street, NW, Seventh Floor, Washington, D.C. 20006.] The effectiveness of oxidative-adulterants is such that they can significantly reduce the uric acid and non-urate markers in a sample. Advantageously, with the embodiments of the subject invention, the reduction in these markers, absent the presence of an adulterant, can still be significantly greater than that seen in adulterated samples and can still reduce the problem of presenting a false positive result. Table 1 illustrates certain drugs and the prevalence of false negative results caused by using oxidant-adulterants.

TABLE 1

Effects of Oxidant Adulterants on Initial and Confirmatory Drug Testing

| | Initial Drug Testing | | | | |
| --- | --- | --- | --- | --- | --- |
| Adulterant | Amphetamines | Cocaine Metabolites | Opiates | Phencylidines | Cannabinoid Metabolites |
| Whizzies, Klear (Nitrite) | − | − | − | − | − |
| Urine Luck (PCC) | − | + | ++ | + | +++ |
| Stealth (H2O2/Peroxidase) | + | + | ++ | + | +++ |

| | Confirmation Drug Testing | | | | |
| --- | --- | --- | --- | --- | --- |
| Adulterant | Methamphetamine | Benzoyecgonine | Morphine | 6-Acetyl Morphine | Phencylidines | Carboxy THC |
| Whizzies, Klear (Nitrite) | − | − | +++ | − | − | +/− |
| Urine Luck (PCC) | − | − | +++ | ++ | − | +++ |
| Stealth (H2O2/Peroxidase) | − | − | +++ | + | − | +++ |

Drug Testing Suppression:
− (<20%);
+ (>20% but <50%);
++ (>50% but <80%);
+++ (>80%) and
+/− (Variable).

Certain embodiments of the subject invention described herein utilize a sodium phosphotungstate reagent for reacting with a urine sample. There are several types phosphotungstate that can be utilized with the embodiments of the subject invention. For example, lithium phosphotungstate could also be used in the embodiments of the subject invention. Preferably, the selected phosphotungstate that is utilized is molybdate-free. A person with skill in the art, having benefit of the subject disclosure, would be able to determine any one of several types of phosphotungstate that could be used in the reagent of the subject invention.

The effects of phosphotungstate can be enhanced by the addition of cyanide to the reagent. While, in one embodiment, the subject invention utilizes a phosphotungstate reagent, other uric acid or non-urate-oxidants could also be used. Non-limiting examples include arsenotungstic acid, arsenophosphotungstic acid, potassium ferricyanide, uranyl acetate, iodine, dichromate, permanganate, and chloramine. A person with skill in the art would be able to determine other indicators that are capable of quantifying the presence of uric acid or non-urate markers by oxidation/reduction, which are capable of being used to practice the subject invention.

A phosphotungstate reagent, according to the subject invention and a General Oxidant Test (DRI® General Oxidant-Detect® Test, ThermoScientific) known in the art were tested on urine samples treated with potential adulterants. Table 2 lists the ingredients of the adulterants tested and adulterant percentage addition to the urine samples.

TABLE 2

Adulterants Used to Characterize Detection

| ADULTERANT TYPE (TRIVIAL NAME) | INGREDIENTS USED TO PREPARE ADULTERANT AND CONCENTRATIONS USED | % ADDED TO SAMPLE |
|---|---|---|
| Stealth | 3% Hydrogen Peroxide + 1,000 Units Peroxidase | 2% |
| Liquid Laundry Bleach | 8.25% Sodium Hypochlorite | 2% |
| Klear, Whizzies | 12.2 g/dL Potassium Nitrite | 10% |
| Urine Luck | pyridium chlorochromate (PCC) 4.31 g/L | 10% |

The General Oxidant Test reagent was used in accordance with the manufacturer's instructions. The product insert states the intended use: "The Test is intended for the detection of urine adulteration by oxidizing compounds" and claims in the product insert that the "test can be performed on any automated clinical chemistry analyzer to detect oxidants". The test utilizes Tetramethybezidine (TMB) as a chromogen in acid solution. The insert further states that "Marijuana samples adulterated with oxidants can produce a positive result, during initial screening by immunoassay, notably the marijuana metabolite (THC). However, the results cannot be confirmed by GC/MS". The product insert does not mention specifically the disappearance of the oxidant over time or indicate what other drugs might be irregular between immunoassay and the confirmatory GC/MS testing.

The General Oxidant Test Reagent insert further states that "Fresh urine specimens should be used" and that the "Mandatory Guidelines for Federal Workplace Drug Testing Programs: Final Guidelines" notice recommends that specimens that do not receive an initial test within 7 days of arrival at the laboratory should be placed into secure refrigeration units.

Figure 4:
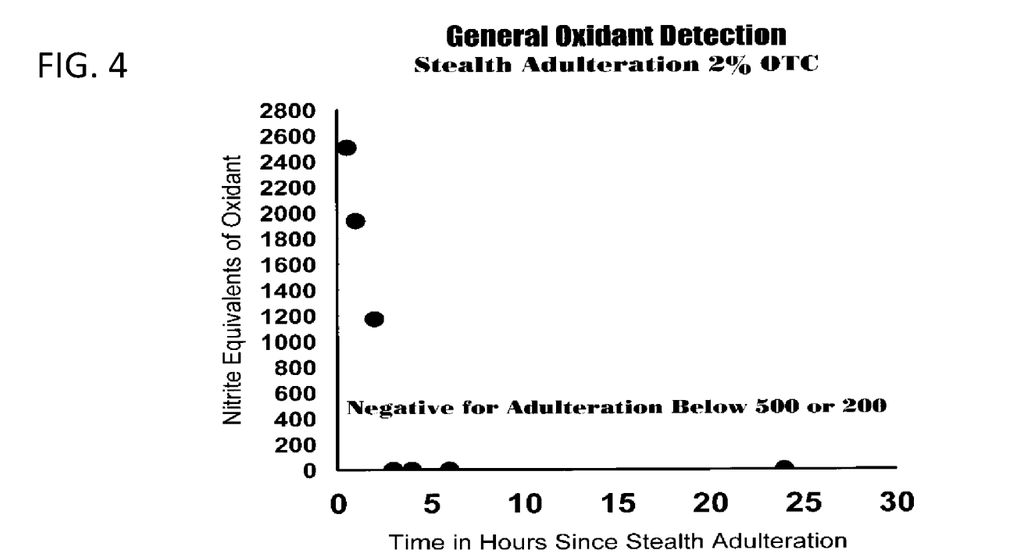
FIG. 4 is a graph that indicates the results obtained with a prior art General Oxidant Test reagent used on a sample adulterated with a Stealth-like adulterant. It can be seen that the nitrite equivalents fell below the accepted absorbance cut-off of 500 µg/mL within a few hours.
Figure 5:
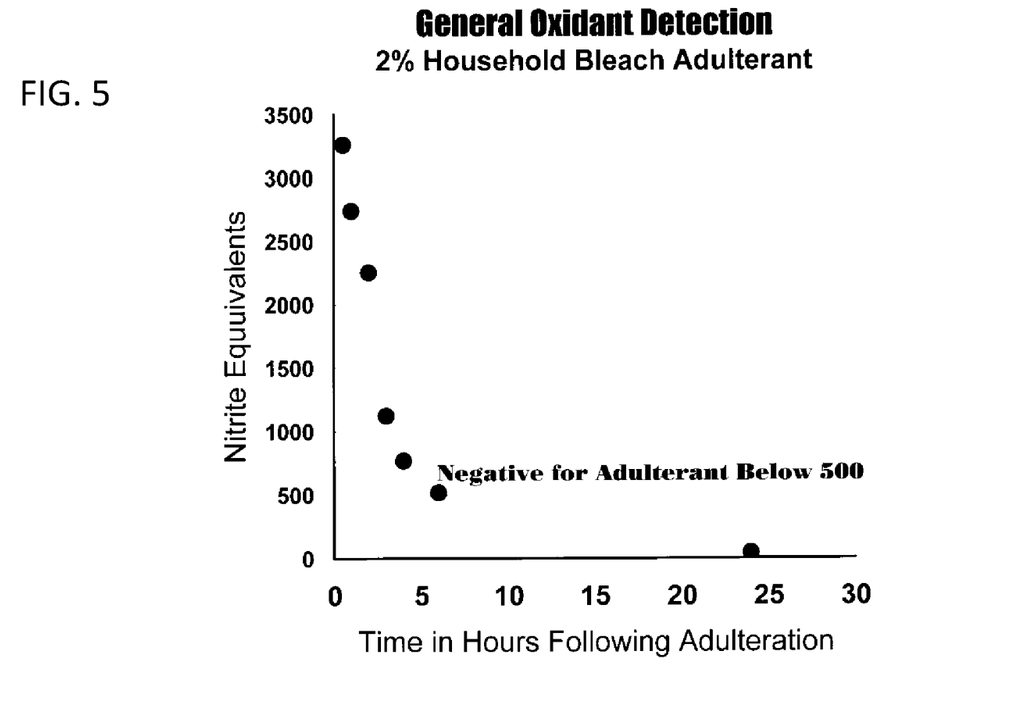
FIG. 5 is a graph that indicates the results obtained with a prior art General Oxidant Test reagent used on a sample adulterated with bleach.
Figure 6:
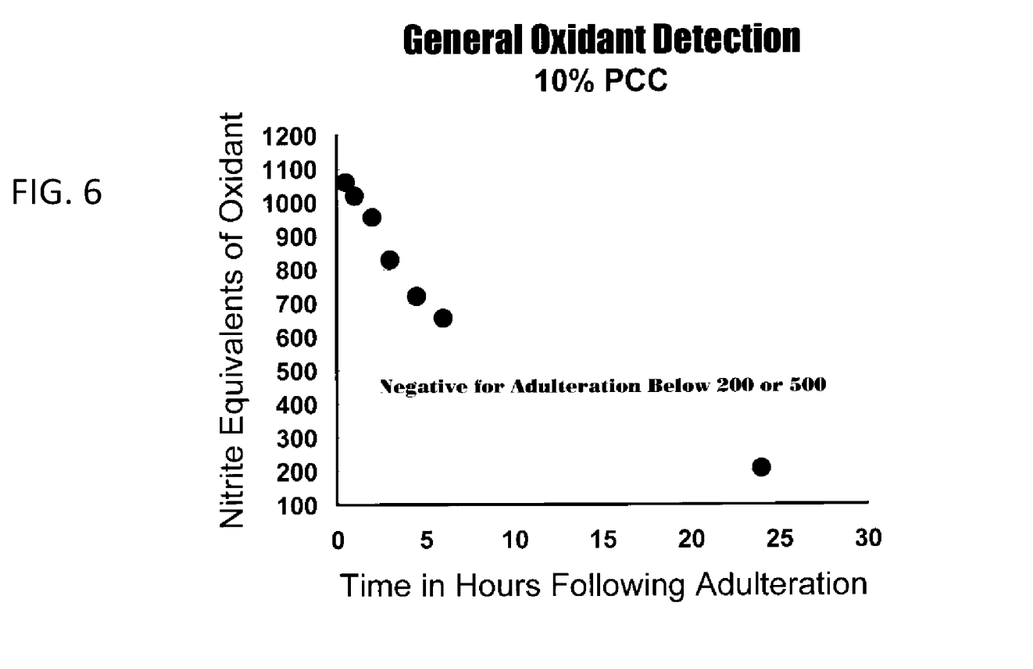
FIG. 6 is a graph that indicates the results obtained with a prior art General Oxidant Test reagent used on a sample adulterated with pyridum chlorochromate (PCC).

FIGS. 4, 5, and 6 show an OHist of the absorbance levels obtained over a span of 24 hours on urine samples adulterated with a Stealth-type, bleach, and pyridium chlorochromate adulterants. The data is plotted as mg/dal Nitrite Equivalents. The tests were calibrated with a 500 m/mL potassium nitrite solution.

For this test, either a 500 µg/mL or 200 µg/mL upper cut-off level is used for positive General Oxidant tests. This is because patients taking certain medications, such as, for example, cardiac drugs, or patients with urinary tract infections, often have nitrite in their urine. Federal Guidelines mandate an oxidant cutoff level at 500 µg/mL. Thus, any samples that exhibit nitrite levels above the cut-off are considered to be potentially adulterated. The insert that is provided with the prior art General Oxidant test states that "urinary nitrite concentrations of 200 µg/mL or greater is . . . proof of adulteration of the specimen."

The OHist determination of the present invention can be calibrated with a reagent containing uric acid. The results can then be reported as Uric Acid Equivalents because the urine-reducing substance acts on both uric acid and non-urate constituents.

Several oxidative-adulterants were tested and an OHist prepared for each sample, according to the subject invention. Pyridium chlorochromate (PCC) did not produce a positive oxidative-adulterant result in a 24 hour period of measurement. While PCC did lower the measurement of Uric Acid Equivalent values, it did not lower values to the accepted cutoff level in the same amount of time as other oxidative adulterants. It is theorized that the PCC may have actually reacted with and destroyed some of the non-urate markers in the urine. This caused a reduction in the concentration of PCC as well as the markers available for measurement, but sufficiently to reach cut-off levels in the given time period. The operation of PCC in the urine over time could result in further destruction of PCC and markers, thus reducing the levels of oxidized markers over time. Consequently, the OHist test method of the subject invention may be require additional time to detect adulteration with PCC. However, a noticeable drop in marker levels over time could warrant further investigation, even if they do not reach cut-off levels.

In contrast to the General Oxidant tests, which, as shown in FIGS. 4-6, are reported as positive for adulteration when results are above a Nitrite Equivalent cutoff, the OHist test of the present invention is positive when the Uric Acid Equivalents are below a Uric Acid Equivalent cutoff level. Although laboratories may choose the cutoff level for the OHist test of the present invention, 20 mg/dL has been chosen for these studies. A cutoff value of, for example, 10 mg/dL of Uric Acid Equivalents could also be used.

To establish a cut-off level, one hundred or more non-adulterated urine samples could be assayed with the phosphotungstate reagent of the subject invention, using a uric acid calibrator to determine the Uric Acid Equivalents of the samples. A mean and a standard deviation of the results can then be calculated. The cutoff value could be, for example, less than 3 standard deviations from the mean. A lower value can be used. The values for males and females should also be calculated separately to determine if there is a gender difference. Also, any sample having a very low value that appears not to be a part of the population may be an adulterated sample and should be excluded from the calculations. Known methods for excluding data such as the 4D Method, the use of t-values, or the Q-Test can be used.

The graph in FIG. 4 indicates that the results obtained with the General Oxidant Test reagent fell below the Nitrite Equivalent cut-off absorbance of 500 µg/mL just a few hours after the sample was treated. Thus, the laboratory results would likely not indicate that this sample was adulterated. Thus, the false negative result produced by the tests for drugs of abuse would be considered accurate. Automated testing is seldom performed in less than an hour and is often performed at least one day following collection of the sample. Thus, the sample would likely be tested well after the adulterant had affected the DOA in the sample. Further, the accepted cut-off levels for nitrite would prevent the sample from being flagged for use of an adulterant. Thus, this sample would not have been subject to confirmatory testing.

Other General Oxidants were tested and the results are shown in FIG. 5 and FIG. 6. FIG. 5 shows the results obtained from a urine sample adulterated with commercial bleach. While common bleach products may not have the notoriety of Stealth, they can be just as effective and can also disappear from the sample as effectively as Stealth. Additionally, a bleach adulterant does not contain peroxidase. Therefore, it is likely that tests used to detect peroxidase-based adulterants will not be effective for detecting bleach.

FIG. 6 shows results obtained from a sample adulterated with pyridium chlorochromate (PCC). PCC disappears, or falls below, the accepted cut-off levels, slower than either Stealth or bleach. However, as mentioned previously, many DOA tests are performed at least 24 hours or longer following sample collection. Thus, even the slow-acting PCC can have sufficient time to destroy the existence of DOA in the sample. Even if the initial test showed positive results, by the time the sample was tested by a confirmatory laboratory, the presence of the PCC would result in a false negative test result and would be accepted as the final result, despite the positive results obtained from the initial screening test.

The current screening tests and procedures utilized to analyze urine samples for DOA can be inaccurate for the detection of adulterants in the sample. Samples that exhibit positive test results can be subject to confirmatory testing, whose results are considered conclusive. However, the confirmatory tests conducted on these samples can also provide inaccurate results because of the time delays often involved before testing samples. Adulterated samples may not be tested before the adulterant in the sample, detected during the initial screening test, has sufficient time to further degrade the evidence of DOA in the urine sample.

The embodiments of the subject invention provide a phosphotungstate reagent and a method of use that can be more accurate than the current reagents and methods used to detect DOA in urine samples. The phosphotungstate reagent can operate by reacting with normally occurring constituents in urine to impart a blue coloration to the sample. Thus, a reduction or lack of blue coloration in a urine sample treated with the phosphotungstate reagent of the subject invention can be an indication of the presence of an oxidative adulterant affecting or inactivating the markers, thus lowering the amount of activation of the chromogen. Further, an OHist can be obtained for samples allowing an initial test result, which may not have been indicative for DOA, to be compared to later test results, which may be indicative of DOA. The results of the OHist can be used as effective evidence of the presence of an oxidative adulterant in a urine sample.

In one embodiment of the method of the subject invention, a urine sample is initially tested by the screening laboratory for DOA, which can include obtaining and recording an initial measurement of the markers to obtain a Uric Acid Equivalents value for the sample utilizing the reagent of the subject invention. However, if the test results show a Uric Acid Equivalents value that is not initially indicative of the presence of an oxidative-adulterant, other tests conducted on the sample may warrant confirmatory testing. In that situation, the sample can be sent to a confirmatory laboratory for further testing. One embodiment of the method of the subject invention includes the confirmatory laboratory conducting further tests of the markers to obtain additional Uric Acid Equivalents values. If the test results of a confirmatory laboratory do not indicate or corroborate the use of DOA for that sample, the one or more Uric Acid Equivalents values can then be compared to the initial Uric Acid Equivalents value obtained by the screening laboratory. All of the Uric Acid Equivalents values can be plotted to create an OHist. If the OHist confirms that the levels of Uric Acid Equivalents values decreased during the time window of the sample, which is from the time the sample was obtained to the time of the confirmatory testing, then the presence or historical presence of an oxidative-adulterant can be definitively confirmed. Consequently, the confirmation of the use of an oxidative-adulterant on the sample can be indicative of the presence or the historical presence of DOA. Procedures dictated by state or federal law can then be initiated.

The scope of the invention is not limited by the specific examples and suggested procedures and uses related herein since modifications can be made within such scope from the information provided by this specification to those skilled in the art.

Following are examples that illustrate procedures for practicing the subject invention. These examples are provided for the purpose of illustration only and should not be construed as limiting. Thus, any and all variations that become evident as a result of the teachings herein or from the following examples are contemplated to be within the scope of the present invention.

EXAMPLE 1

Reagents and Methods of Use, Including Obtaining an Oxidant History (OHIST)

A. Reagent Preparation:

Reagent 1: Phosphotungstate Reagent—1 Liter: Add 27 grams of molybdenum free sodium tungstate to approximately 333 mL deionized water in a reflux vessel. Add 30.9 grams of phosphoric acid. Add boiling chips and reflux gently for 2 hours. Cool to room temperature and then dilute to 1 Liter with deionized water. Add 21.0 grams of Lithium Sulfate and mix.

All ingredients are ACS grade. Molybdinum free Sodium Tungstate was obtained from GFS Chemicals, Powell Ohio 43065. The reagent so prepared is stable for at least 1 year refrigerated at 2-8 degrees Celsius.

Reagent 2: Carbonate Buffer Reagent—1 Liter. Dissolve 119 grams of ACS grade sodium carbonate to 800 mL of deionized water. Add 7.5 grams sodium hydroxide. Add deionized water to bring the volume to 1 Liter. This reagent is used to buffer the test sample and blank.

The reagent is stable for at least 1 year at ambient temperature 20-30 degrees Celsius.

Reagent 1 and 2 are stable for at least 1 year when packaged together and stored at 2-8 degrees Celsius.

Reagent 3: Uric acid 40 mg/dL Calibrator: 1 Liter—Dissolve 0.63 grams of ACS grade lithium carbonate in 500 mL of Deionized water. Warm to about 45 degrees Celsius. The mixture should not be warmer than 50 degrees Celsius for the next step. Add 400 mg of ACS grade uric acid and mix until dissolved. Dissolve 0.5 grams of sodium azide and then dilute to 1 liter with deionized water.

This calibrator is stable for at least 1 year refrigerated at 2-8 degrees Celsius.

B. Oxidative-adulterant Assay Method:
Manual Method: Test—Add 100 µL of Urine Sample to 2 mL of Phosphotungstate Test Reagent 1 and mix.
Reagent Blank —Add 100 µL of Deionized water to 2 mL of Phosphotungstate Reagent 1 and mix.
Add 1 mL of Carbonate Buffer Reagent 2 to Reagent Blank and Test Reagent and mix each one separately.
Incubate for 5 minutes at 37 degrees Celsius.
Measure absorbance at 700 nm of Reagent Blank and Test Reagent.
Calibrator absorbance is developed by using the calibrator as a Test.
The Test Net absorbance (Test Absorbance-Blank Absorbance) is used to calculate the Uric Acid Equivalent result as follows:

(Test Net Absorbance/Calibrator Net Absorbance)×
Calibrator Absorbance=Value of Calibrator The absorbance measurement may be made at 600-700 nm. No secondary bichromatic wavelength should be used.
C: Automated Measurement Parameters:
1. Mindray BS200 Clinical Analyzer Parameters:
Test: OX Hist
No. User Defined
Full Name: Oxidant History
Reaction Type: Endpoint
Pri. Wave 670 nm
Sec Wave none
Direction: Increase
Reac. Time: 0 and 11
Incubation Time: 3
Unit: Mg/dL UAEq
Precision: Integer
R1: 18
R2: 90
Sample Volume; 10
Mixed Reagent Blank: Optional
Compensate: Slope:1 Intercept: 0
2. AU 400, AU 400e, AU 480, AU 640, AU640e and AU680 Series Clinical Analyzers Parameters.
Reagent ID: User defined
Test Name: Oxidant History
Sample Volume: 10
R1 Volume: 100
R2 Volume: 50
Wavelength: Pri: 700 Sec. None
Method: END
Reaction Slope: +
Measuring Point 1: First 25 Last 27
Measuring Point 1: (Not Applicable)
Calibration Type: AA Formula: Y=AX +B

EXAMPLE 2

Procedures for Obtaining an Oxidant History (OHIST)

The reagents and methods of automation described in Example 1, above, can be used to exploit the kinetics of Uric Acid Equivalents measurement by performing a screening test on a urine sample soon after collection and then repeating the screening test hours or even days following the first test. For example, the collecting site or first immunoassay screening laboratory can test the sample and obtain an initial Uric Acid Equivalents value for the sample. If the initial value concludes the possible presence of an adulterant, the results can be reported to the confirmatory laboratory. The confirmatory laboratory can also obtain one or more Uric Acid Equivalent values on the same sample. The results of the initial Uric Acid Equivalents value can be compared with the results of the one or more Uric Acid Equivalents values obtained by the confirmatory laboratory. If analysis of the Uric Acid Equivalents values shows a reduction in the values over time, the presence of an oxidative-adulterant can be considered definitive proof of the use of an oxidative-adulterant in the sample. Even if the analysis of the Uric Acid Equivalents values do not fall below the mandated cutoff level indicative for positive adulteration, adulteration can still be definitively proven if the Uric Acid Equivalents values obtained from confirmatory laboratory tests have fallen significantly during the time window of the sample.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

The invention has been described herein in considerable detail, in order to comply with the Patent Statutes and to provide those skilled in the art with information needed to apply the novel principles, and to construct and use such specialized components as are required. However, the invention can be carried out by specifically different equipment and devices, and that various modifications, both as to equipment details and operating procedures can be effected without departing from the scope of the invention itself. Further, although the present invention has been described with reference to specific details of certain embodiments thereof and by examples disclosed herein, it is not intended that such details should be regarded as limitations upon the scope of the invention except as and to the extent that they are included in the accompanying claims.

The invention claimed is:
1. A method for detecting a presence of an oxidative-adulterant in urine utilizing a reagent system comprising:
a first reagent comprising phosphotungstate;
a second reagent comprising sodium carbonate;
wherein the method comprises:
adding the first reagent to the urine to form a test reagent;
adding the second reagent to the test reagent to form a buffered test reagent;
utilizing a spectrophotometer to measure an absorbance of the buffered test reagent;
calculating a Uric Acid Equivalents value based on the measure of absorbance;
comparing the Uric Acid Equivalents value to a pre-determined value;
and determining the presence of an oxidative-adulterant in the urine when the Uric Acid Equivalents value is below the pre-determined value.
2. The method, according to claim 1, wherein the pre-determined value is 10 mg/dl.

3. The method, according to claim 2, further comprising incubating the buffered test reagent for a pre-determined time prior to measuring the absorbance of the buffered test reagent.

4. The method according to claim 3, further comprising configuring an automated clinical analyzer to measure the absorbance of the buffered test reagent.

5. The method according to claim 4, further comprising a third reagent comprising uric acid that is diluted and used to calibrate the clinical analyzer prior to measuring absorbance of the buffered test reagent.

6. The method according to claim 5, wherein absorbance is measured at between 580 nm and 800 nm.

7. The method according to claim 6, wherein absorbance is measured at 700 nm.

8. A method for obtaining an Oxidant History for a sample of urine, comprising:
utilizing a reagent system comprising:
　a first reagent comprising phosphotungstate;
　a second reagent comprising sodium carbonate;
wherein the method comprises,
　(a) adding the first reagent to the urine to form a test reagent;
　(b) adding the second reagent to the test reagent to form a buffered test reagent;
　(c) utilizing a spectrophotometer to measure an absorbance of the buffered test reagent;
　(d) calculating a Uric Acid Equivalents value based on the measure of absorbance;
　(e) reanalyzing the buffered test reagent, after a pre-determined time, to obtain a subsequent measure of absorbance; and
　(f) calculating a subsequent Uric Acid Equivalents value based on the subsequent measure of absorbance; such that the Uric Acid Equivalents value and the subsequent Uric Acid Equivalents value constitute an Oxidant History for the urine.

9. The method, according to claim 8, wherein a Uric Acid Equivalents value or a subsequent Uric Acid Equivalent value that is below 10 mg/dl indicates oxidative-adulteration of the urine.

10. The method, according to claim 8, further comprising incubating the buffered test reagent for a pre-determined time prior to obtaining the measure of absorbance of the buffered test reagent.

11. The method according to claim 10, further comprising configuring an automated clinical analyzer to measure the absorbance of the buffered test reagent.

12. The method according to claim 11, further comprising a third reagent comprising uric acid that is diluted and used to calibrate the clinical analyzer prior to measuring absorbance of the buffered test reagent.

13. The method according to claim 12, wherein absorbance is measured at between 580 nm and 800 nm.

14. The method according to claim 13, wherein absorbance is measured at 700 nm.

15. The method according to claim 8, further comprising comparing the subsequent Uric Acid Equivalents value to the Uric Acid Equivalents value, wherein the subsequent Uric Acid Equivalents value being less than the Uric Acid Equivalents value indicates that the urine was adulterated with an oxidant.

16. The method according to claim 8, wherein steps (e) through (f) are repeated over a period of time to obtain additional Uric Acid Equivalent values for the Oxidant History, such that a decrease in the Uric Acid Equivalent values over time indicates that the urine was adulterated with an oxidant.

\* \* \* \* \*

UNITED STATES PATENT AND TRADEMARK OFFICE
CERTIFICATE OF CORRECTION

| | | |
|---|---|---|
| PATENT NO. | : 10,571,457 B2 | Page 1 of 1 |
| APPLICATION NO. | : 16/139802 | |
| DATED | : February 25, 2020 | |
| INVENTOR(S) | : Jerry W. Denney | |

It is certified that error appears in the above-identified patent and that said Letters Patent is hereby corrected as shown below:

In the Specification

<u>Column 15,</u>
Line 34, "R1: 18" should read --R1: 180--.

Signed and Sealed this
Twenty-eighth Day of July, 2020

Andrei Iancu
*Director of the United States Patent and Trademark Office*